United States Patent [19]

Wanzenböck

[11] Patent Number: 5,727,940
[45] Date of Patent: Mar. 17, 1998

[54] DENTAL HEAD GEAR

[75] Inventor: Karl Wanzenböck, Leobersdorf, Austria

[73] Assignee: Fildan Accessories Corporation, Englewood, N.J.

[21] Appl. No.: 727,078

[22] Filed: Oct. 8, 1996

[51] Int. Cl.[6] .................................................. A61C 3/00
[52] U.S. Cl. ............................................. 433/5; 24/68 CD
[58] Field of Search ........................... 433/5; 24/68 CD, 24/68 SK, 68 R, 625, 602, 71.1

[56] References Cited

U.S. PATENT DOCUMENTS

| | | |
|---|---|---|
| 4,215,983 | 8/1980 | Frazier ........................................... 433/5 |
| 4,226,589 | 10/1980 | Klein .............................................. 433/5 |
| 4,553,934 | 11/1985 | Armstrong et al. ......................... 433/5 |
| 4,718,848 | 1/1988 | Hickham et al. ............................ 433/5 |
| 4,872,836 | 10/1989 | Grove ............................................ 433/5 |
| 5,205,020 | 4/1993 | Kamper .................................. 24/68 CD |
| 5,511,975 | 4/1996 | Schendell .................................... 433/5 |

Primary Examiner—John J. Wilson
Attorney, Agent, or Firm—Herbert Dubno

[57] ABSTRACT

A dental headgear having a traction generating device around which a loop of a strap is passed and having a pair of springs which maintain the traction and a connecting member which can automatically pull out from the housing when a maximum tension is exceeded.

18 Claims, 5 Drawing Sheets

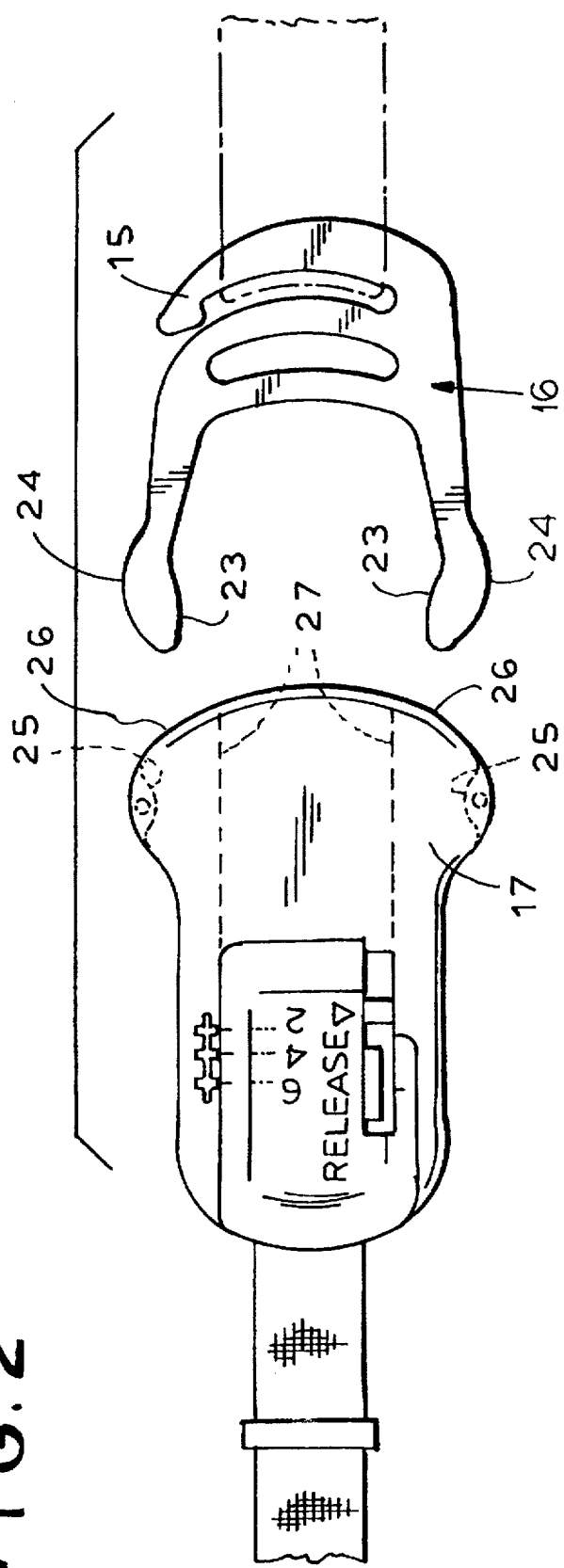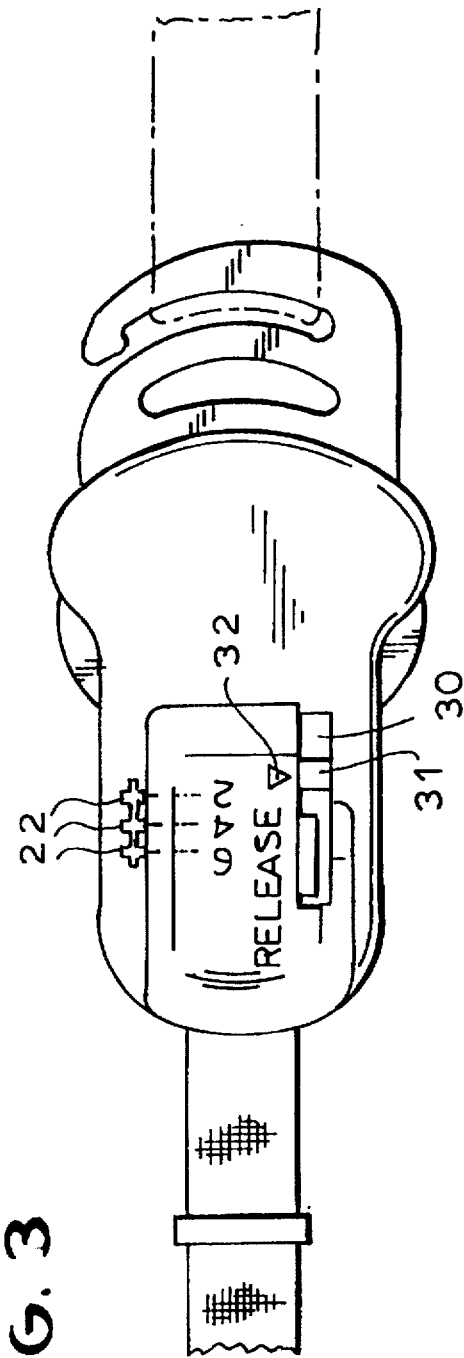

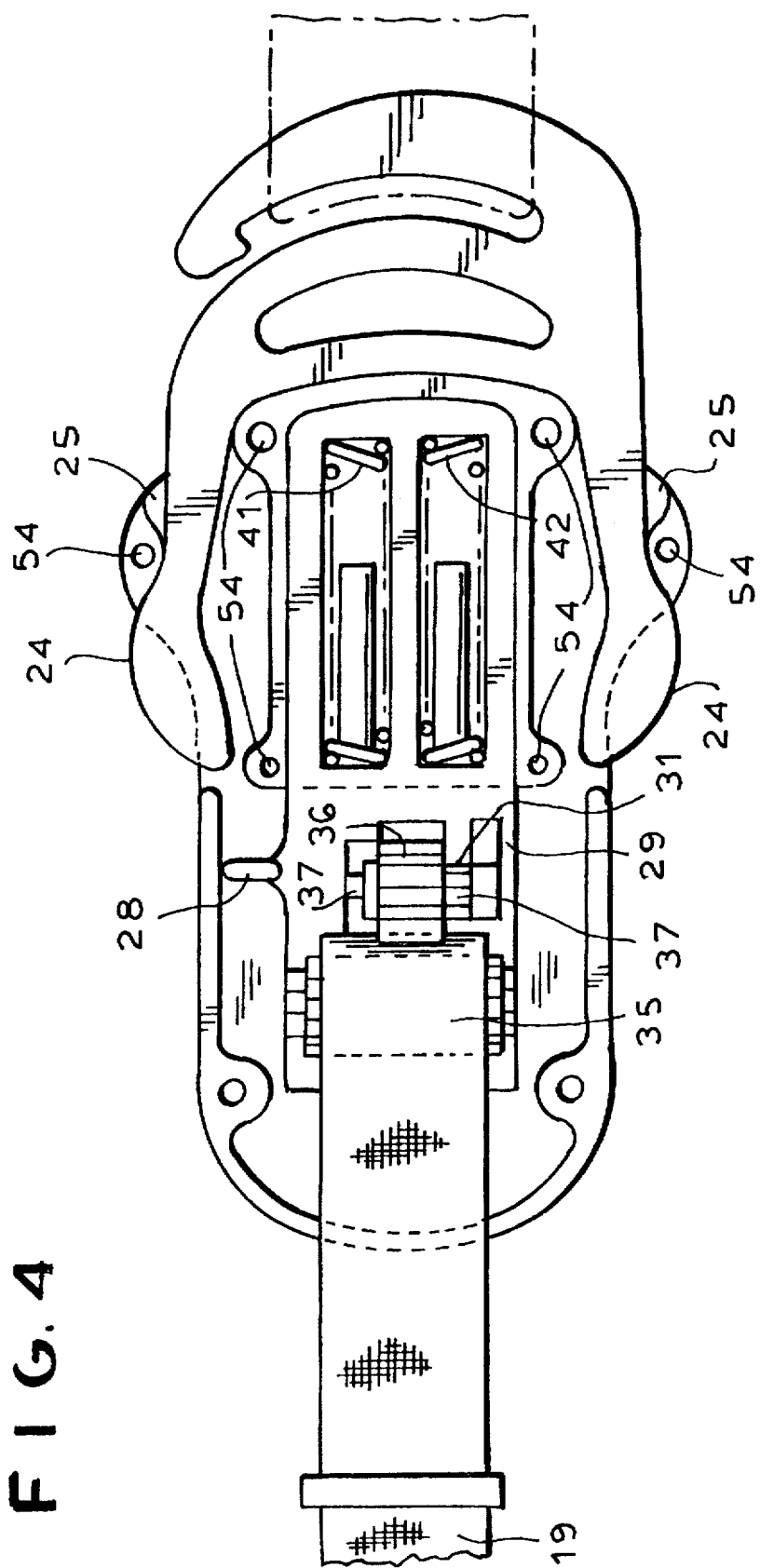

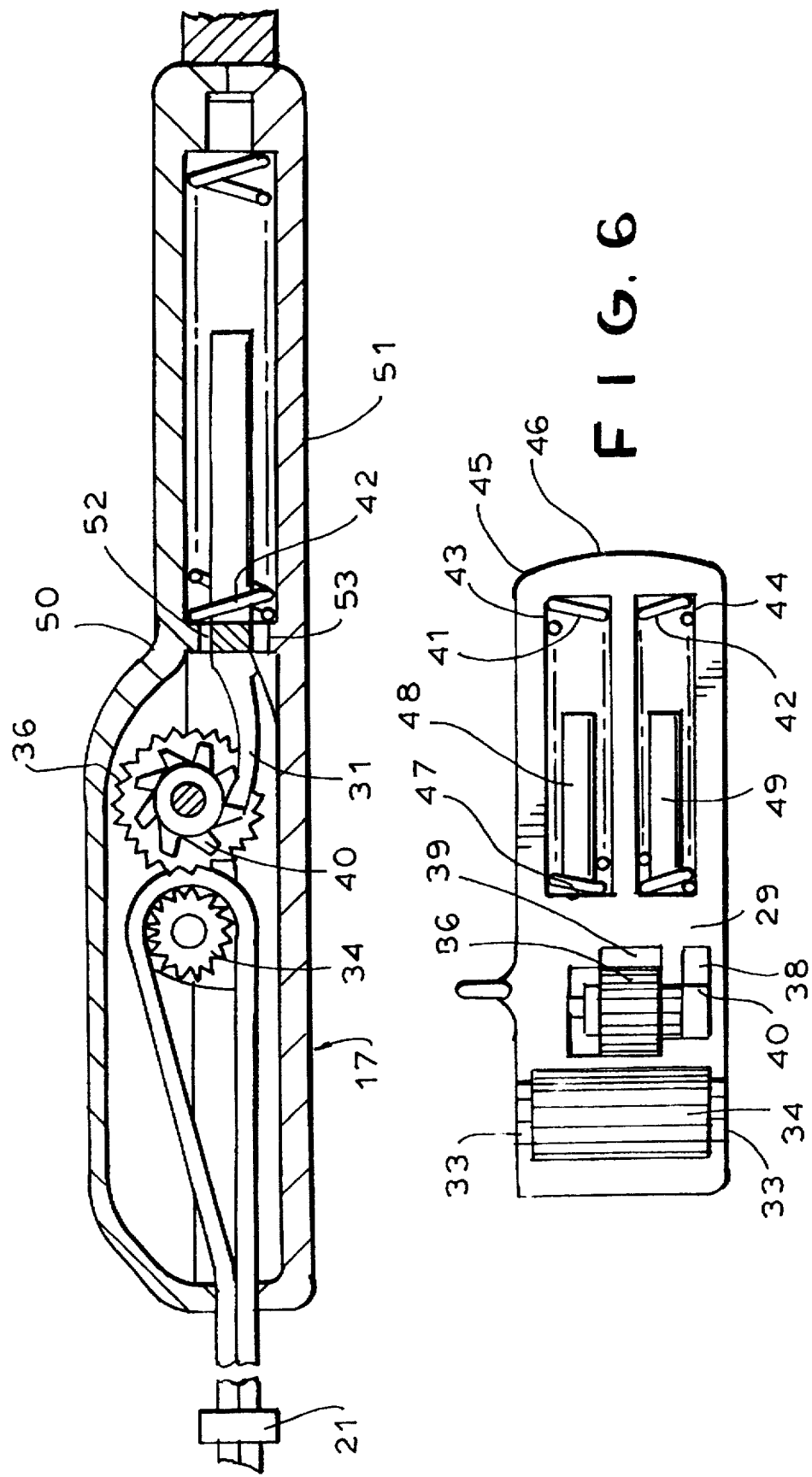

5,727,940

DENTAL HEAD GEAR

FIELD OF THE INVENTION

The present invention relates to a dental headgear and regulator system of the type in which a head piece is connected by at least one and usually two tension-generating devices via respective tension straps to a dental regulator or retainer which presses against the teeth of the patient in order to apply an inward pressure thereto.

More particularly this invention concerns the tension-generating device.

BACKGROUND OF THE INVENTION

Dental headgear are known which have a device of the type described utilizing a spring to apply tension to a strap which, in turn, pulls upon the dental regulator or retainer to apply pressure to the teeth of the patient.

In the past, such devices have proved to be disadvantageous in that the spring could not be readily set to generate a precise tension and required repeated adjustments.

This was not only time consuming, but frought with the danger that an improper force would be applied to the teeth at any point in time. Furthermore, it has long been recognized that the application of excessive force with such dental headgear is problematical and hence earlier devices have been designed to release upon the development of excessive force. The release mechanisms used also were not fully reliable and accurate with respect to the force threshold at which the release occurred.

OBJECTS OF THE INVENTION

Accordingly, it is the principal object of the present invention to provide an improved dental headgear which is free from the drawbacks of earlier devices and can generate desired tensions in the straps for the retainer or regulator with greater precision than has hitherto been the case.

Another object of the invention is to provide a simple and economical construction for such dental headgear which can insure precise release of tension should the tension exceed a given threshold.

Another object of the invention is to provide an improved dental headgear which overcomes disadvantages of earlier systems and yet is economical, simple, reproducible in action and comparatively inexpensive.

A further object of the invention is also to provide a traction or tension-generating device which is more precise than earlier devices which have been used in dental headgear.

SUMMARY OF THE INVENTION

These objects and others which will become more apparent hereinafter are attained, in accordance with the invention in a dental headgear comprising:

a harness adapted to seat upon the head of a wearer;
a traction-generating device connected to the headpiece;
a tension strap connected to the device; and
a dental regulator for applying pressure to the teeth of the wearer connected to the tension strap, the traction-generating device comprising:
a housing member,
a slide member in the housing member,
a pair of mutually parallel springs braced against the housing member and the slide member and resiliently resisting displacement of the slide member relative to the housing member, and
means for connecting one of the members to the tension strap and the other of the members to the harness for maintaining the tension strap under a tension established by the springs.

According to a feature of the invention, a coupling member is fitted into the housing member and includes a tongue engageable in a slot of the housing member open in a direction opposite that from which the strap extends from the device, the tongue being formed by a pair of resilient arms which are biased inwardly upon insertion of the coupling member into the housing member, the ends of the arms having protuberances behind which engage inwardly projecting formations of the housing member to retain the coupling member against tensions below the aforementioned threshold. The coupling member can be connected to the harness which fits about the head of the wearer while the strap is connected to the dental retainer or regulator.

When a tension is applied which exceeds the threshold, the coupling member readily pulls out of the housing to release the connection between the harness and the strap and thereby relieve the tension.

The protuberances can be outwardly convex rounded surfaces which are readily cammed inwardly when the coupling member is pulled from the housing member. Advantageously, when the coupling member is in place within the housing member, the arms straddle the slide member so that the slide member and the arms can lie in a common plane and contribute to the flatness of the unit. The coupling member can have a hook engageable with the harness.

According to a feature of the invention, the strap is connected to the slide member by a loop of the strap which passes around a toothed roller while a toothed pressure wheel likewise journalled on the slide member can bear against the strap and can have a ratchet wheel which is held against reverse rotation by a pawl formed as a tongue of the slide member. When the free end of the strap is pulled, the ratchet wheel rotates and the slide member is drawn toward the retainer to increase the tension, the loop being retained by the engagement of the pawl with a tooth of the ratchet wheel. Only upon the depression of the pawl to release it from the ratchet wheel can the strap loop be pulled in the opposite direction to decrease the tension.

The housing member can have an opening affording access to the finger on the pawl which is provided for releasing it from the ratchet wheel.

Alternatively, instead of a ratchet wheel, a pivotal toothed locking member can be provided which, in one position, allows the strip to be drawn through the tension device and around the toothed roller and which, in another position, locks the strap against the toothed roller. An arm portion of this latter eccentric locking member can be engaged by a finger of the user to release the strap so that the device can be further tightened or loosened to suit the pressure intended against the teeth.

According to another feature of the invention, a window is provided in the housing member and indicia are provided along this window while the slide member has an index which can be viewed through this window so that the actual tension generated by the device can be ready.

The slide member can have a frame within which the springs are disposed and the springs can be braced against a limb of this frame proximal to the harness and against a ledge of the housing member. It has been found, quite surprisingly, that the provision of two parallel springs can completely eliminate one of the major drawbacks of earlier traction-generating devices for dental headgear and utilizing only a single spring, namely, the variation from time to time of the tension generated in a particular device and the lack of reproducibility from device to device in spite of the fact that the springs may derive from the same manufacturer's lot.

When two identical parallel coil springs are used in place of a single spring, the variability from device to device is found to be practically eliminated and precise tensions can be generated over long periods of time with the device because of the presence of the two springs which appear to average out any variation in response to compression.

The system of the invention is thus highly effective for dental headgear and eliminates a major drawback of earlier devices for the purposes described.

The invention also comprises a tension-generating device which comprises:

a housing member;

a slide member in a housing member;

a pair of mutually parallel springs pressed against the housing member and the slide member and resiliently resisting displacement of the slide member relative to the housing member; and means for connecting said members to elements between which a tension is to be generated by the springs.

BRIEF DESCRIPTION OF THE DRAWING

The above and other objects, features, and advantages will become more readily apparent from the following description, reference being made to the accompanying drawing in which:

FIG. 2 is a diagrammatic elevational view showing the automatic release of the coupling member from the housing of the traction-generating device;

FIG. 3 is a view similar to FIG. 2 showing the coupling member attached to the remainder of the traction-generating device;

FIG. 4 is a view of the traction-generating device in the position shown in FIG. 3 but with the cover removed;

FIG. 5 is a longitudinal section through the traction generating device of FIG. 4;

FIG. 6 is an elevational view of the slide of the traction-generating device;

SPECIFIC DESCRIPTION

Figure 1:
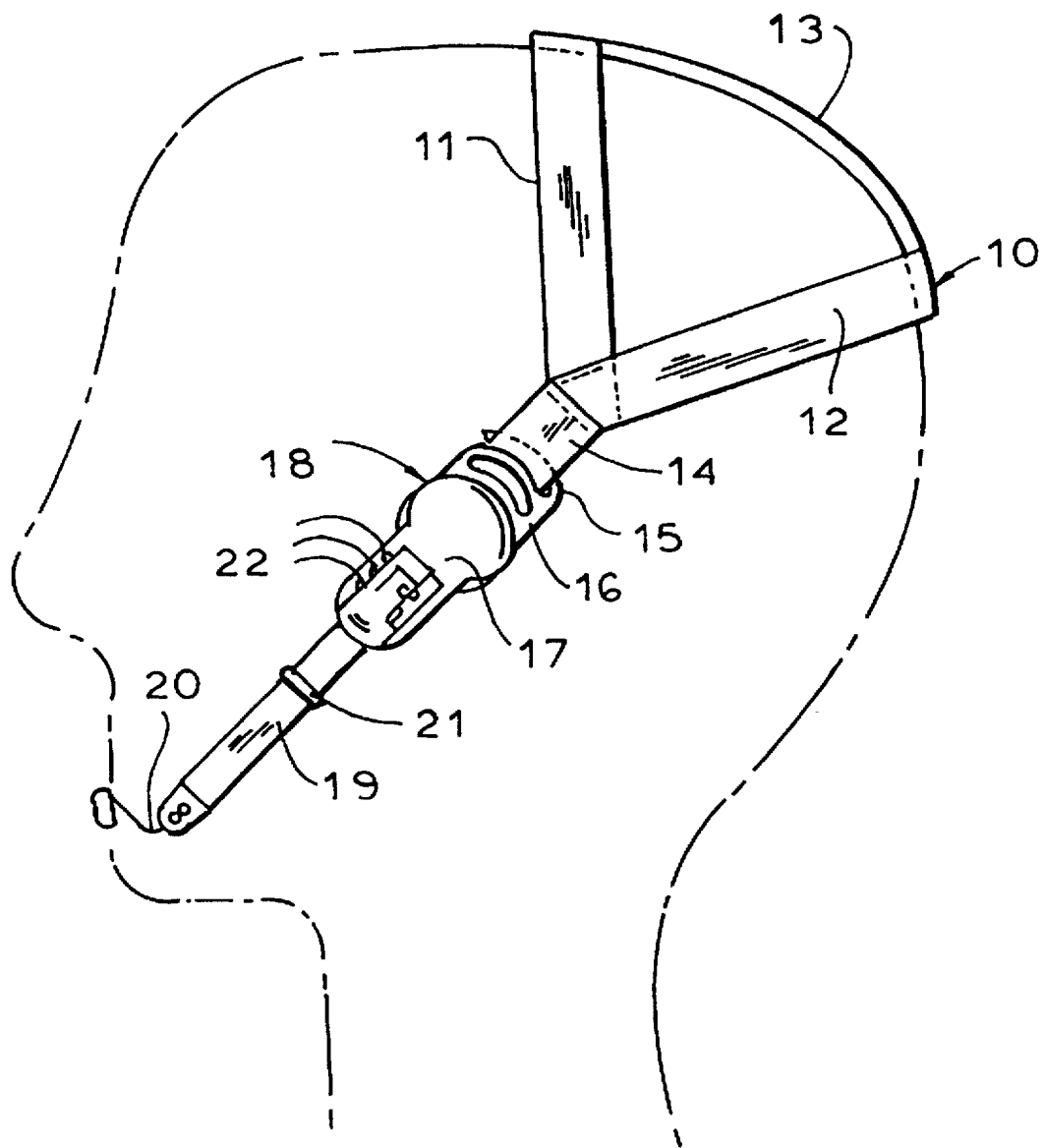
FIG. 1 is an elevational view of one side of a dental headgear provided with a tension device according to the invention and showing its application to the dental headgear, the harness, straps and dental regulator being conventional in the art.

As can be seen generally in FIG. 1, a dental headgear according to the invention can include a harness 10 which fits around the back of the head of the user and can comprise a pair of straps 11 and 12 which extend around the head from one side to the other, and a further strap 13 which can lie in a saggital plane. On each side of the head, these straps are connected to a loop 14 which engages in a hook 15 of a coupling member 16 engaged in a housing 17 of a tension-generating device 18 from which a strap 19 extends to the dental regulator 20 which is braced against the teeth of the wearer in an effort to correct the tooth orientation in an orthodontic procedure. The strap 19 and the retainer 20 are also conventional in the art.

Also visible in FIG. 1 are an eye 21 through which the strap 19 passes from the loop within the tension-generating unit 18 and the marks 22 on the latter which signal the tension applied to the strap 19 and thus the force applied to the dental regulator 20.

From FIGS. 2 and 3, it will be apparent that the coupling member 16 with its hook 15 is formed with a pair of arms 23 constituting a tongue having rounded protuberances 24 which can engage inwardly of a pair of projections 25 of the housing 17 which is open at its right hand end at 26 to form channels 27 in which the arms 23 can engage. The projections 25 engage behind the protuberances 24 and, when an excessive force is produced by the tension-generating device, the arms 23 are deflected inwardly and coupling member 16 can automatically pull out of the housing 17 (compare FIG. 3 with FIG. 2). This force can be accurately preset to provide the automatic release which is required as has been described above.

Visible also in FIGS. 2 and 3 is the fact that the markings 22 are openings in the cover of the housing 17 through which a pointer (index) 28 (FIG. 4) is visible, the pointer 28 being provided on a slider 29. The pointer 28 can have a contrasting color, e.g. red when the housing 17 is white, black or blue, for example.

From FIGS. 2 and 3 it can be seen further that the housing is formed with an opening 30 through which a pawl 31, which will be described in greater detail hereinafter, is exposed so that it can be displaced out of engagement with the ratchet to release the latter. The location at which a point can be inserted through the window 30 into engagement with the pawl has been indicated by a mark 32 designated for "release" of the device.

Turning now to FIGS. 4–6, it will be apparent that the slider 29 is formed with a pair of trunions 33 on which a toothed roller 34 is journaled, a loop 35 of the strap 19 passing over this toothed roller and being engaged by a toothed wheel 36 which is, in turn, journaled on the slider 29 with trunions 37. The pawl 31 previously mentioned is defined in the material of the slider 29 by openings 38 and 39 on opposite sides thereof. The pawl 31 engages a ratchet wheel 40 forming part of the pressure wheel 36. When the pawl 31 is pressed downwardly, therefore, the ratchet wheel 40 is released and the strap 19 is free to pass around the toothed roller 34. To increase the tension on the dental regulator 20, however, the free end of the strap 19 is pulled to rotate the toothed roller 34 in the counterclockwise sense, thereby driving the pressure roller 36 in the clockwise sense (FIG. 5), permitting the teeth of the ratchet 40 to skip passed the pawl 31 which prevents reverse rotation until the pawl 31 is pressed downwardly. The slider 29 is thereby drawn to the left (FIGS. 4–6), increasing the tension upon the strap until the desired tension is reached as measured by the location of the pointer 28 in one of the openings 22 which can be calibrated in terms of hundreds of grams of tension, for example.

The tension is maintained by a pair of compression coil springs 41, 42 received within respective windows 43 and 44 of a frame 45 forming part of the slider. The springs 42 are braced upon a limb 46 of the frame and an intermediate part 47 of the slider and are prevented from blowing out of the window by fingers 48 and 49 molded to form part of the slider and extending part way through the coil springs.

When the unit of FIG. 6 is inserted into the housing 17, between the upper or cover member 50 and the base member 51, the springs 41 and 42 can engage ledges 52 and 53 of members 50 and 51 so that, when the slider is drawn to the left, the springs 41 and 42 are pressed between the frame limb 46 and the ledges 52 and 53. The housing members 50 and 51 are aligned by pins 54 to facilitate assembly.

In operation with respect to the device of FIGS. 1–6, the harness is placed upon the wearer and the dental regulator is fitted to the mouth and each of the straps 19 on the other side is pulled to progressively increase the tension which is displayed through the openings 22. When the desired tension is reached, the pawl 31 prevents back rotation of the wheel 36 and the strap loop is thus locked while the compressed springs 41 and 42 maintain the tension. Should it be necessary to relieve the tension, a point can be inserted to deflect the pawl 31 downwardly (FIG. 5) thereby allowing the wheel 36 to rotate in the counterclockwise sense and the spring force to be relieved. The application of excessive force is prevented because upon exceeding the threshold of maximum force, the arms 23 will be deflected inwardly and will pull out from behind the projections 25.

Figure 7:
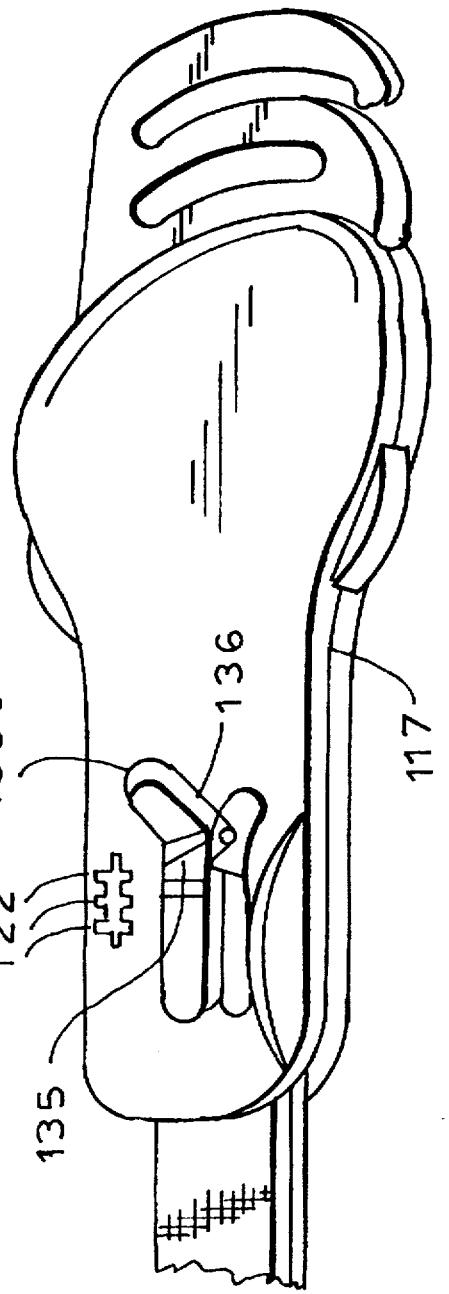
FIG. 7 is a diagrammatic perspective view of another traction-generating device utilizing a locking lever rather than a ratchet wheel for locking the strap against the toothed roller.

In the embodiment of FIG. 7, which is generally similar to that of FIGS. 1–6, instead of a pressure wheel 36, an eccentric lock is provided to prevent the loop 135 of the strap 119 from slipping and the toothed wheel 134 from rotating. In this embodiment the slider 129 has an eccentric lock 136 which is swingable between the trunions 137 (only one of which is visible in FIGS. 7–9) and can be rotated from the position shown in FIG. 8, in which a thin finger 136a lightly engages the loop 135 to permit the strap to be drawn in either direction but to be retained against involuntary loosening, and a position shown in FIG. 9 in which two more massive teeth 136b press tightly against the loop 135 and the wheel 134 to prevent any movement of the strap relative to the slider.

Figure 9:
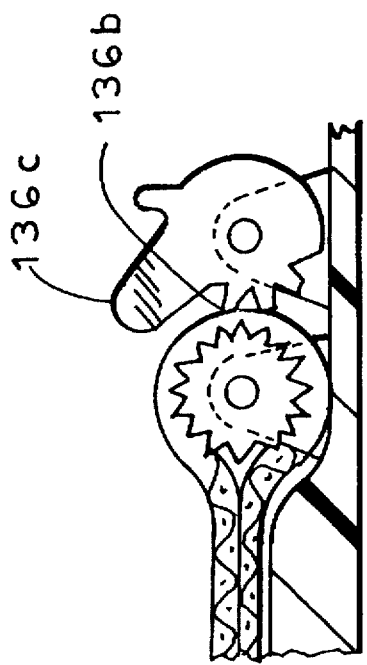
FIG. 9 is a view similar to FIG. 8 showing the locked position thereof.
Figure 8:
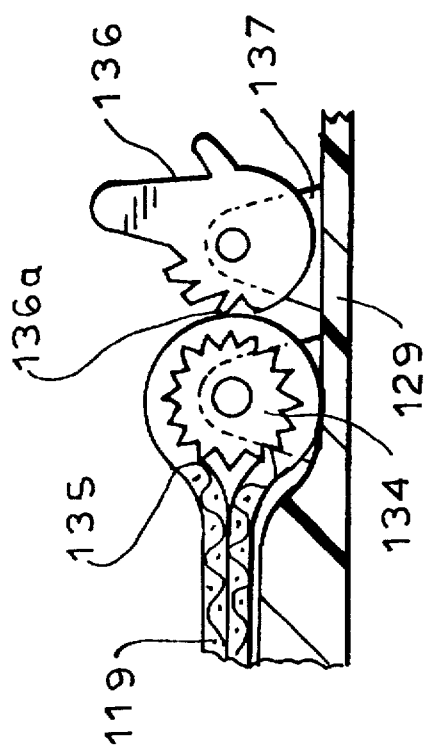
FIG. 8 is a diagrammatic section showing the unlocked position of the lever.

A lever arm 136c projects from a window 136d in the housing 117 so that it can be swung between the positions shown in FIGS. 8 and 9 by the wearer. Otherwise the device of FIGS. 7–9 operates similarly to that of FIGS. 1–6 displaying the force on the regulator, e.g. through the openings 122. While the locking of the strap relative to the slider in the embodiment of FIGS. 1–6 is automatic, here it is effected by swinging member from the position shown in FIG. 8 to the position shown in FIG. 9.

I claim:

1. A dental headgear comprising:
   a harness adapted to seat upon the head of a wearer;
   a traction-generating device connected to said headpiece;
   a tension strap connected to said device; and
   a dental regulator for applying pressure to the teeth of the wearer connected to said tension strap, said traction-generating device comprising:
   a housing member,
   a slide member in said housing member,
   a pair of mutually parallel springs braced against said housing member and said slide member and resiliently resisting displacement of said slide member relative to said housing member, and
   means for connecting one of said members to said tension strap and the other of said members to said harness for maintaining said tension strap under a tension established by said springs, said means for connecting including a roller around which said strap is looped and an eccentric locking member swingable between a position in which said strap is locked against said roller and a position in which said strap can advance around said roller.

2. The dental headgear defined in claim 1 wherein said means for connecting includes a coupling member engageable in said housing member and having a pair of resiliently deflectable arms provided with outwardly bulging protuberances and receivable in said housing member, said housing member being formed with a slot receiving said coupling member and having a pair of inwardly projecting formations engageable behind said protuberances whereby, upon application of tension to said device exceeding a predetermined value, said arms are cammed inwardly by said formations and slide past said formations to enable said coupling member to separate from said housing.

3. The dental headgear defined in claim 2 wherein said protuberances are rounded.

4. The dental headgear defined in claim 3 wherein said coupling member is formed in one piece with said arms and a hook engageable with said harness.

5. The dental headgear defined in claim 1 wherein said slide member is provided with an indexing element visible through an opening in said housing member and cooperating with indicia representing different tensions for displaying a tension applied to said strap.

6. The dental headgear defined in claim 1 said pressure wheel is connected with a rachet wheel, said slide member having a pawl engageable with said rachet wheel for preventing reverse rotation of said pressure wheel, said roller and said pressure wheel being mounted on said slide member, said pawl having a finger exposed through an opening in said housing member enabling deflection of said pawl away from said rachet wheel for release of tension of the device.

7. The dental headgear defined in claim 6 wherein said protuberances are rounded.

8. The dental headgear defined in claim 7 wherein said coupling member is formed in one piece with said arms and a hook engageable with said harness.

9. The dental headgear defined in claim 7 wherein said slide member is provided with an indexing element visible through an opening in said housing member and cooperating with indicia representing different tensions for displaying a tension applied to said strap.

10. The dental headgear defined in claim 7 wherein said slide member is provided with a frame defining an opening, said housing member having a ledge at an end of said opening proximal to said strap, said springs being coil compression springs receivable in said opening and braced against said ledge.

11. A dental headgear comprising:
    a harness adapted to seat upon the head of a wearer;
    a traction-generating device connected to said headpiece;
    a tension strap connected to said device; and
    a dental regulator for applying pressure to the teeth of the wearer connected to said tension strap, said traction-generating device comprising:
    a flat housing member,
    a slide member in said housing member,
    a pair of mutually parallel springs braced against said housing member and said slide member and resiliently resisting displacement of said slide member relative to said housing member, and means for connecting one of said members to said tension strap and the other of said members to said harness for maintaining said tension strap under a tension established by said springs, said slide member being provided with a flat frame defining an opening, said housing member having a ledge at an end of said opening proximal to said strap, said springs being coil compression springs receivable in said opening and braced against said ledge.

12. A dental headgear comprising:

a harness adapted to seat upon the head of a wearer;

a traction-generating device connected to said headpiece;

a tension strap connected to said device; and a dental regulator for applying pressure to the teeth of the wearer connected to said tension strap, said traction-generating device comprising:

a housing member, a slide member in said housing member, a pair of mutually parallel springs braced against said housing member and said slide member and resiliently resisting displacement of said slide member relative to said housing member, and means for connecting one of said members to said tension strap and the other of said members to said harness for maintaining said tension strap under a tension established by said springs, said means for connecting including a roller around which said strap is looped and a toothed pressure wheel pressing against the strap on said roller, a sleeve fitting around said strap and receiving an end of said strap turned back over said strap from said loop.

13. The dental headgear defined in claim 12 said pressure wheel is connected with a ratchet wheel, said slide member having a pawl engageable with said ratchet wheel for preventing reverse rotation of said pressure wheel, said roller and said pressure wheel being mounted on said slide member, said pawl having a finger exposed through an opening in said housing member enabling deflection of said pawl away from said rachet wheel for release of tension of the device.

14. A dental headgear comprising:

a harness adapted to seat upon the head of a wearer;

a traction-generating device connected to said headpiece;

a tension strap connected to said device; and a dental regulator for applying pressure to the teeth of the wearer connected to said tension strap, said traction-generating device comprising:

a housing member, a slide member in said housing member, a pair of mutually parallel springs braced against said housing member and said slide member and resiliently resisting displacement of said slide member relative to said housing member, and means for connecting one of said members to said tension strap and the other of said members to said harness for maintaining said tension strap under a tension established by said springs, said housing member being connected to said head gear and said strap being connected to said slide member, said means for connecting including a roller around which said strap is looped and a toothed pressure wheel pressing against the strap on said roller, a sleeve fitting around said strap and receiving an end of said strap turned back over said strap from said loop, and a coupling member engageable in said housing member and having a pair of resiliently deflectable arms provided with outwardly bulging protuberances and receivable in said housing member, said housing member being formed with a slot receiving said coupling member and having a pair of inwardly projecting formations engageable behind said protuberances whereby upon application of tension to said device exceeding a predetermined value, said arms are cammed inwardly time need formation and slide past said formations to enable said coupling member to separate from said housing.

15. A tension generating device which comprises:

a flat housing member;

a slide member in a housing member;

a pair of mutually parallel springs pressed against the housing member and the slide member and resiliently resisting displacement of the slide member relative to the housing member; and means for connecting said members to elements between which a tension is to be generated by said springs, said slide member being provided with a flat frame defining an opening, said housing member having a ledge at an end of said opening proximal to said strap, said springs being coil compression springs receivable in said opening and braced against said ledge.

16. The tension-generating device defined in claim 15 wherein:

said housing member is formed at one end thereof with a slot, said means for connecting including a coupling member having a pair of inwardly deflectable arms receivable in said slot, said housing member having inwardly projecting formations engageable behind outwardly bulging protuberances on said arms, whereby said coupling member separates from said housing member upon the development of a tension greater than a predetermined tension across said device.

17. The device defined in claim 16 wherein said means for connecting includes a strap extending into said housing member at an opposite end thereof and forming a loop in said housing member, said slide member being provided with a toothed roller around which said loop extends, a toothed pressure wheel engaging said strap at said loop, a rachet wheel connected to said pressure wheel, a tongue on said slide member forming a pawl engageable with said rachet wheel, and a finger on said pawl exposed through an opening in said housing member to enable deflection of said pawl away from said rachet wheel.

18. The device defined in claim 16, further comprising an index on said slide member, a window formed in said housing member through which said index can be viewed, and indicia on said housing member cooperating with said index to display a tension generated by said device.

* * * * *